US00PP35426P2

(12) United States Plant Patent
Smith

(10) Patent No.: US PP35,426 P2
(45) Date of Patent: Oct. 17, 2023

(54) ***CHRYSANTHEMUM* PLANT NAMED 'CIFZ0101'**

(50) Latin Name: ***Chrysanthemum* x *morifolium***
Varietal Denomination: CIFZ0101

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/109,318

(22) Filed: Feb. 14, 2023

(51) Int. Cl.
*A01H 5/02* (2018.01)
*A01H 6/14* (2018.01)

(52) U.S. Cl.
USPC ..... Plt./289
CPC ..... *A01H 6/1424* (2018.05)

(58) Field of Classification Search
USPC ..... Plt./289, 290, 295, 296
CPC ..... A01H 5/02
See application file for complete search history.

*Primary Examiner* — Kent L Bell
(74) *Attorney, Agent, or Firm* — Dale Skalla

(57) ABSTRACT

A new garden type *Chrysanthemum* plant named 'CIFZ0101' particularly distinguished by its large size plant with mound plant habit, a medium size decorative flower, orange to yellow flower color and a natural season response early October.

1 Drawing Sheet

Figure 1:
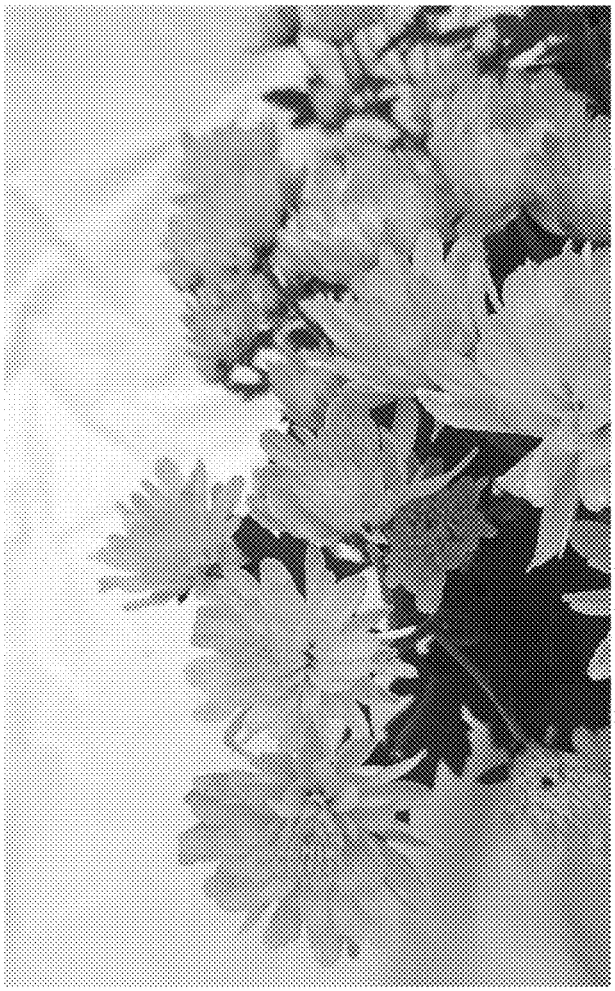

Latin name of the genus and species of the plant claimed: *Chrysanthemum* x *morifolium.*

Varietal denomination: 'CIFZ0101'.

BACKGROUND OF THE NEW PLANT

The present invention comprises a new *Chrysanthemum*, botanically known as *Chrysanthemum* x *morifolium,* and hereinafter referred to by the variety name 'CIFZ0101'.

'CIFZ0101' is a product of a planned breeding program. The new cultivar has large size plant with mound plant habit, a medium size decorative flower, orange to yellow flower color and a natural season response early October 'CIFZ0101' originated from a mutation of X-ray treated cuttings in November 2019 in Fort Myers, Fla. 'CIFZ0101' was selected from the resulting plants on Mar. 20, 2020 in Alva, Fla.

The sport parent was a proprietary seedling 'FC0116', not patented.

TABLE 1

Characteristics of the female parent, compared to 'CIFZ0101':

| | 'CIFZ0101' | 'FC0116' |
|---|---|---|
| Natural response | 3 days faster | 2 days slower |
| Blackcloth response | 2 days faster | 2 days slower |
| Flower size | Similar | Similar |
| Flower color | Orange to yellow | Pink/Lavender |
| Flower type: | Similar | Similar |
| Plant size: | Similar | Similar |
| Plant habit: | Similar | Similar |

'CIFZ0101' differs from 'CIFZ0102' (Co-pending U.S. Plant patent application Ser. No. 18/109,324) and 'CIFZ0103' (Co-pending U.S. Plant patent application Ser. No. 18/109,327) in at least ray floret color.

As the new variety is the result of mutation breeding, there is not a male parent.

The first act of asexual reproduction of 'CIFZ0101' was accomplished when vegetative stem cuttings were propagated from the initial selection in May 2020 in Alva, Fla.

BRIEF SUMMARY OF INVENTION

Horticultural examination of plants grown from cuttings of the plant initiated in May 2020 and continuing thereafter, has demonstrated that the combination of characteristics as herein disclosed for 'CIFZ0101' are firmly fixed and are retained through successive generations of asexual reproduction.

'CIFZ0101' has not been observed under all possible environmental conditions. The phenotype may vary significantly with variations in environment such as temperature, light intensity and day length.

A Plant Breeder's Right for this cultivar has not yet been applied for. 'CIFZ0101' has not been made publicly available prior to the effective filing date of this application, notwithstanding any disclosure that may have been made less than one year prior to the effective filing date of this application by the inventor or another who obtained 'CIFZ0101' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0101' with colors being as true as possible with an illustration of this type.

Figure 2:
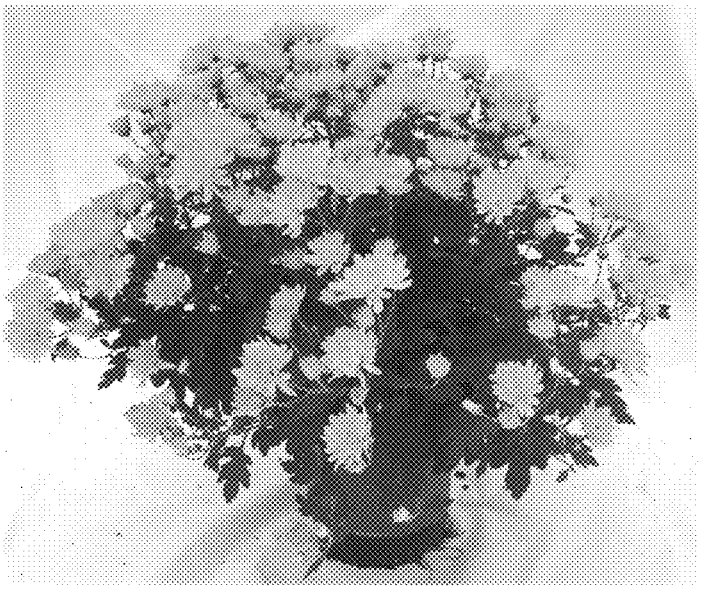

The photographic drawings show in FIG. 1 a close view of flowers of the new variety and in FIG. 2 a flowering plant from an outdoor trial.

The aforementioned photographs: FIG. 1, as well as FIG. 2 were taken on Sep. 5, 2022 both showing a plant from the same blackcloth outdoor trial in Enkhuizen, The Netherlands.

These plants were about 13 weeks of age. One rooted cutting per pot had been planted in a 19 cm pot, not pinched in week 23, 2022 and black clothed from week 29. Plants started flowering the end of August 2022.

The measurements were taken in Enkhuizen, The Netherlands, in September 2022 on plants from the same outdoor blackcloth trial.

DETAILED BOTANICAL DESCRIPTION

Color references are made to The Royal Horticultural Society Colour Chart (RHS) 2001.

TABLE 2

DIFFERENCES BETWEEN THE NEW VARIETY 'CIFZ0101' AND TWO MOST SIMILAR VARIETIES:

| | 'CIFZ0101' | 'CIFZ0051', U.S. Plant Pat. No.29,540 |
|---|---|---|
| Natural response: | ½ week faster in warm nights | ½ week slower in warm nights |
| Blackcloth response: | 3 days faster | 3 days slower |
| Flower size: | Larger | Smaller |
| Flower color: | Similar | Similar |
| Flower type: | Similar | Similar |
| Plant size: | Bit larger | Bit smaller |
| Plant habit: | Similar | Similar |

TABLE 3

| | 'CIFZ0101' | 'PPP AMIK 09', U.S. Plant Pat. No. 21,453 |
|---|---|---|
| Natural response: | Similar but ½ week faster in Florida | Similar but ½ week slower in Florida |
| Blackcloth response: | Almost 1 week faster | Almost 1 week slower |
| Flower size: | Smaller | Larger |
| Flower color: | Similar | Similar |
| Flower type: | Similar | Similar |
| Plant size: | Larger | Smaller |
| Flower longevity: | Less fade | More fade |
| Flowering uniformity: | More uniform | Less Uniform |

Plant:

*Form, growth and habit.*—Herbaceous garden-type, stems Upright and outwardly spreading, freely branching, strong and rather vigorous growth habit.

*Plant height* (*above soil*).—22 cm.

*Plant height* (*inflorescence included*).—24 cm.

*Plant width.*—43 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 137A.

*Immature leaf, color lower surface.*—RHS 137B.

*Mature leaf, color, upper surface.*—RHS 137A.

*Mature leaf, color lower surface.*—RHS 137C.

*Length.*—4.5 cm.

*Width.*—3.2 cm.

*Shape.*—Ovate, with distinct lobes.

*Base shape.*—Attenuate.

*Apex shape.*—Apiculate.

*Margin.*—3 lobed.

*Number of margin indentations.*—8-9.

*Depth of margin indentations.*—2-5 mm.

*Leaf length terminal lobe relative to total leaf length.*—1:2.5.

*Leaf depth lower lateral sinus.*—1.6 cm.

*Texture, upper surface.*—Bifid hairs.

*Texture, lower surface.*—Bifid hairs.

*Color of veins, upper surface.*—RHS 137C.

*Color of veins, lower surface.*—RHS 137C.

*Pattern of veining.*—Palmate.

*Petiole color.*—RHS 137C.

*Petiole length.*—1.8-2.5 cm.

*Diameter.*—0.2 cm.

*Texture.*—Bifid hairs.

*Presence of stipules.*—No.

Stem:

*Quantity of main branches per plant.*—6-8.

*Color of stem.*—RHS 138B.

*Length of stem.*—13.0-15.0 cm.

*Diameter.*—0.3 cm.

*Length of internodes.*—1.2-1.6 cm.

*Texture.*—Bifid hairs.

*Color of peduncle.*—RHS 138B.

*Length of peduncle.*—3.0-3.7 cm.

*Peduncle diameter.*—0.2 cm.

*Texture.*—Bifid hairs.

Inflorescence:

*Type.*—Compositae, solitary, decorative inflorescences borne terminally above foliage, elliptical ray florets arranged in whorls on a capitulum giving a double flower.

*Quantity of short days to flowering.* (*response time*).—Approximately 6.5 weeks.

*Quantity of inflorescences per plant.*—About 90 with several small buds developing.

*Lastingness of individual blooms on the plant.*—About six weeks from first color.

*Fragrance.*—Slightly spicy.

Bud (when showing color):

*Color.*—RHS 13B.

*Length.*—0.7 cm.

*Width.*—0.5 cm.

*Shape.*—Oblate.

Immature inflorescence (at moment of opening):

*Diameter.*—2.5 cm.

*Color of ray florets, upper surface.*—RHS 17B.

*Color of ray florets, lower surface.*—RHS 16B.

Mature inflorescence:

*Diameter.*—3.5 cm.

*Depth.*—1.6 cm.

*Total diameter of disc.*—0.3-0.4 cm.

*Receptacle color.*—RHS 147B.

*Receptacle height.*—0.3 cm.

*Receptacle diameter.*—1.1 cm.

*Length of corolla tube.*—0.1 cm.

Ray florets:
*Average quantity of florets.*—80-95.
*Color of florets, upper surface.*—RHS 14B.
*Color lower surface.*—RHS 16C.
*Length.*—1.5 cm.
*Width/diameter.*—0.5 cm.
*Shape.*—Elliptical.
*Apex shape.*—Dentate.
*Base shape.*—Tube.
*Margin.*—Entire. Small incisions may be present at tip.
*Margin: type of rolling.*—Moderately involute.
*Texture, upper surface.*—Papillate.
*Lower surface.*—Papillate.
*Ribs present.*—Yes.
*Number of keels.*—2.
*Profile at widest point.*—Flat.
*Longitudinal axis shape.*—Sinusoidal.
*Longitudinal axis curvature strength.*—Weak.
*Corolla tube shape.*—Circular.

Disc florets:
*Number of disc florets.*—20-30.
*Width.*—0.1 cm.
*Length.*—1.0 cm.
*Color.*—RHS 14A.

Inflorescence (at moment of senescence):
*Color of ray florets, upper surface.*—RHS 21A.
*Color of ray florets, lower surface.*—RHS 16C.

Phyllaries:
*Quantity.*—20-24.
*Color, upper surface.*—RHS 147B.
*Color, lower surface.*—RHS 137A.
*Length.*—0.6-1.0 cm.
*Width.*—0.2 cm.
*Shape.*—Lanceolate.
*Apex shape.*—Acute.
*Base.*—Fused.
*Margins.*—Entire.
*Texture, upper surface.*—Glabrous.
*Texture, lower surface.*—Canescent.

Reproductive organs:
*Pistil.*—One.
*Length.*—0.4 cm.
*Style color.*—RHS 5C.
*Style length.*—0.3 cm.
*Stigma color.*—RHS 5C.
*Stigma shape.*—Bi-parted.
*Ovary color.*—RHS 157C.
*Ovary length.*—0.2 cm.
*Ovary width.*—0.1 cm.

Androecium:
*Stamens.*—1, found on only disc florets.
*Color of filaments.*—RHS 157C.
*Length filaments.*—0.2 cm.
*Anther color.*—RHS 14A.
*Anther length.*—0.2 cm.
*Anther shape.*—Oval to club shaped.
*Color of pollen.*—RHS 14A.
*Pollen amount.*—Sparse.
*Fertility/seed set.*—Has not been determined to date.
*Disease/pest resistance.*—Has not been determined to date.
*Hardiness.*—Has not been determined to date.

What is claimed is:

1. A new and distinct variety of *Chrysanthemum* plant named 'CIFZ0101' substantially as illustrated and described herein.

* * * * *